(12) United States Patent  
Elsenhans et al.

(10) Patent No.: US 8,100,007 B2  
(45) Date of Patent: Jan. 24, 2012

(54) METHOD AND APPARATUS FOR DETECTING CONTACT OF A PIPETTING NEEDLE WITH A LIQUID IN A VESSEL

(75) Inventors: Olivier Elsenhans, Sins (CH); Ulrich Opara, Erfstadt (DE); Vuk Siljegovic, Mettmenstetten (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/570,319

(22) Filed: Sep. 30, 2009

(65) Prior Publication Data

US 2010/0077853 A1    Apr. 1, 2010

Related U.S. Application Data

(63) Continuation of application No. PCT/EP2008/001667, filed on Mar. 3, 2008.

(30) Foreign Application Priority Data

Mar. 30, 2007 (EP) .................................. 07006665

(51) Int. Cl.
*G01F 23/296* (2006.01)
(52) U.S. Cl. ..................................... 73/290 V; 116/227
(58) Field of Classification Search .................. 73/290 V
See application file for complete search history.

(56) References Cited

U.S. PATENT DOCUMENTS 4,954,997 A * 9/1990 Dieulesaint et al. ............ 367/13
5,705,750 A * 1/1998 Mizukami et al. .............. 73/602

FOREIGN PATENT DOCUMENTS

| DE | 3737204 A1 | 5/1989 |
| EP | 0732598 A1 | 9/1996 |
| EP | 1111351 A2 | 6/2001 |
| FR | 2628527 A1 | 9/1989 |
| FR | 2761153 A1 | 9/1998 |
| WO | 93 25914 | 12/1993 |
| WO | WO 9843053 A1 * | 10/1998 |

OTHER PUBLICATIONS

International Search Report, Appl. No. PCT/EP2008/001667, Jun. 26, 2008.

* cited by examiner

*Primary Examiner* — Hezron E Williams
*Assistant Examiner* — Paul West
(74) *Attorney, Agent, or Firm* — Dinsmore & Shohl LLP

(57) ABSTRACT

A method and level sensor apparatus for detecting contact of a pipetting needle with at least a liquid contained in a vessel are disclosed. The apparatus provides a pipetting needle made of a material suitable for transmitting ultrasonic waves, a needle holder for holding the needle, a electromechanical transducer for generating ultrasonic pulses to be transmitted towards the needle, for receiving echo pulses reflected at the tip of the needle, and for generating an electrical output signal representative of the echo pulses, and electronic circuit means for generating and applying a driving signal to the transducer, which generates corresponding pulses which are transmitted to the needle towards the tip thereof, and for monitoring and evaluating the output signal to detect the position of the needle at which the tip of the needle contacts the liquid and for providing a resulting signal representative of the result of said evaluation.

30 Claims, 14 Drawing Sheets

METHOD AND APPARATUS FOR DETECTING CONTACT OF A PIPETTING NEEDLE WITH A LIQUID IN A VESSEL

CROSS REFERENCE TO RELATED APPLICATIONS

The present application is filed under 35 U.S.C. §111(a) as a continuation of copending International Application No. PCT/EP2008/001667, with an international filing date of Mar. 9, 2008, and claims priority under 35 U.S.C. §119 to European Patent Application No. 07006665.9, filed Mar. 30, 2007.

TECHNICAL FIELD

The described embodiments of the invention concern a method and a level sensor apparatus for detecting contact of a pipetting needle with a liquid contained in a vessel.

The described embodiments of the invention further concern a pipetting apparatus for pipetting liquid volumes into and from a liquid contained in a vessel by means of a pipetting needle, and the latter apparatus comprises a level sensor apparatus of the above mentioned kind.

BACKGROUND

Liquid level detection plays an important role for automated chemical analyzers and provides better control of the pipetting process. For performing pipetting operations, a pipetting needle contacts liquid contained in a vessel either for aspirating a sample thereof or for delivering a volume of another liquid to the liquid in the vessel. In order to reduce carry over and to achieve the desired accuracy of a pipetting system it is necessary to minimize contact of the pipetting needle with a vessel's content. For this purpose it is desirable to minimize the penetration depth of the tip of the pipetting needle in the liquid. Liquid level detection plays an important role for this purpose.

Most liquid level detection methods are reliable under normal circumstances but fail when operation of the pipetting systems includes piercing of a vessel's closure with the pipetting needle or when the pipetting needle encounters foam before it reaches the surface of a liquid contained in a vessel.

In the case of liquid vessels closed with a cover, usually used for storage of reagents, the level sensor of the pipetting system should be able to detect a liquid level that lies under a cover or closure (membrane, foil) of the vessel. A capacitive level sensor, widely used in chemical analyzers, does not work properly in that case and erroneously indicates detection of a liquid surface when it meets a wet cover. Capacitive liquid detectors also often erroneously detect foam lying on a liquid surface as if it were a liquid level.

SUMMARY

A first aim of the invention is therefore to provide a method and a level sensor apparatus which make possible to reliably detect contact of a pipetting needle with a liquid contained in a vessel and thereby reliable determine the position of the pipetting needle at which the tip thereof contacts the free surface of that liquid.

According to a first aspect of the invention the above mentioned first aim is reached with a method for detecting contact of the tip of a pipetting needle with a liquid contained in a vessel, the detecting being effected within a time interval during which the pipetting needle is moved towards the liquid in the vessel for performing a pipetting operation, and a level sensor apparatus for detecting contact of a pipetting needle with a liquid contained in a vessel.

The method comprises applying ultrasonic pulses to the pipetting needle by means of a electromechanical transducer which is mechanically connected to a part of the needle which is located at a predetermined distance from the tip of the pipetting needle; transmitting through the pipetting needle mechanical pulses generated by the application of the ultrasonic pulses to the pipetting needle; the transmitting of mechanical pulses including transmission of mechanical pulses generated by the transducer towards the tip of the pipetting needle and also transmission in the opposite sense of mechanical pulses reflected at the tip; receiving the reflected mechanical pulses with the electromechanical transducer, the electromechanical transducer thereby generating a corresponding electrical output signal; and monitoring the electrical output signal, selecting at least one specific component thereof by means of a time-of-flight or signal phase analysis, and by evaluating the variation with time of predetermined characteristics of a parameter of the at least one selected component of the output signal in order to detect the position of the needle at which the pipetting needle contacts the free surface of the liquid contained in the vessel and for providing a resulting signal representative of the result of the evaluation.

The level sensor apparatus comprises a pipetting needle made of a material suitable for transmitting ultrasonic waves and having at one end a tip through which liquid is pipetted; a needle holder for holding the pipetting needle; an electromechanical transducer which is mechanically connected to the pipetting needle, the electromechanical transducer being apt to generate ultrasonic pulses to be transmitted to the pipetting needle), to receive echo pulses reflected at the tip of the needle, and to generate an electrical output signal representative of the echo pulses; and electronic circuit means connected with the electromechanical transducer, the electronic circuit means comprising electrical signal generating means for generating a driving signal and for applying this signal to the electromechanical transducer, which generates corresponding ultrasonic pulses which are transmitted to the pipetting needle towards the tip thereof, and electrical signal processing means for receiving and processing the electrical output signal of the electromechanical transducer, for selecting at least one a specific component of the output signal by means of a time-of-flight or signal phase analysis, and for evaluating the variation with time of predetermined characteristics of a parameter of the at least one selected component of the output signal in order to detect the position of the needle at which the tip of the pipetting needle contacts the free surface of the liquid contained in the vessel and for providing a resulting signal representative of the result of the evaluation; and transport means for automatically transporting the needle holder and the needle, for positioning the needle at a pipetting position and for moving the tip of the needle towards the free surface of the liquid contained in the vessel.

According to the invention ultrasonic pulses are transmitted through the pipetting needle and pulses reflected at the fluid delivery tip of the pipetting needle are detected. It should be noted that this approach clearly differs from systems wherein continuous wave ultrasound is used. Ultrasonic pulses are generated e.g. by applying pulses of short duration of an electrical signal having a suitable frequency to a piezoelectric transducer. Continuous wave ultrasound is generated e.g. by applying an electrical signal having a constant amplitude and a suitable frequency to a piezoelectric transducer.

The main advantages of the method and the level sensor apparatus according to the invention is that by applying ultrasonic pulses instead of continuous waves it is possible to use the time of flight of an ultrasonic pulse to determine the contact and the position or distance at which contact occurs between the transmitting material, in this case the pipetting needle, and any external object or medium. Moreover it is possible to determine also the presence of eventual anomalies of the needle itself. The above mentioned first aim can therefore be achieved even if the pipetting needle has to pierce a cover of the vessel in order to reach the liquid surface, and even if the pipetting needle has to pass through foam in order to reach the liquid surface. Moreover, the determination of the position of the pipetting needle when the tip thereof contacts the free surface of the liquid achieved with the method and the level sensor apparatus according to the invention makes possible to control the transport of the pipetting needle in such a way that the penetration depth of the tip of the needle in the liquid contained in the vessel is minimized.

A second aim of the invention is to provide a level sensor apparatus which in addition makes it possible to verify whether a pipetting needle is present or absent in a pipetting apparatus, whether such a pipetting needle has a deformation or whether there is an undesirable contact of the pipetting needle with a body.

According to a second aspect of the invention the above mentioned second aim is achieved with embodiments of the level sensor apparatus wherein means for evaluating a variation with time of at least one of amplitude and phase of at least one selected component of an output signal is provided, and comprise means for detecting changes of the amplitude or phase of a reflected ultrasonic wave and for generating an output signal which corresponds to discontinuities within the needle or contact of the needle with an external object or medium.

A third aim of the invention is to provide a level sensor apparatus which in addition makes it possible to measure the depth of penetration of the tip of the needle in the liquid contained in the vessel.

According to a third aspect of the invention the above mentioned third aim is achieved with embodiments of the level sensor apparatus wherein means for evaluating a variation with time of at least one of amplitude and phase of at least one selected component of an output signal is provided and comprise means for detecting changes of the amplitude or phase of a reflected ultrasonic wave and for generating an output signal which corresponds to the depth of penetration of the tip of the needle in the liquid contained in the vessel.

A fourth aim of the invention is to provide a pipetting apparatus for reliably pipetting liquid volumes into and from a liquid contained in a vessel by means of a pipetting needle and even if foam lies above the liquid and/or a cap closes an opening of the vessel and has to be pierced by the pipetting needle in order to carry out a pipetting operation.

According to a fourth aspect of the invention the above mentioned fourth aim is achieved with a pipetting apparatus for pipetting liquid volumes into and from a liquid contained in a vessel by means of a pipetting needle, the apparatus comprising a level sensor apparatus embodiment according to the present invention.

BRIEF DESCRIPTION OF THE DRAWINGS

The subject invention will now be described in terms of its preferred embodiments with reference to the accompanying drawings. These embodiments are set forth to aid the understanding of the invention, but are not to be construed as limiting.

Figure 1:
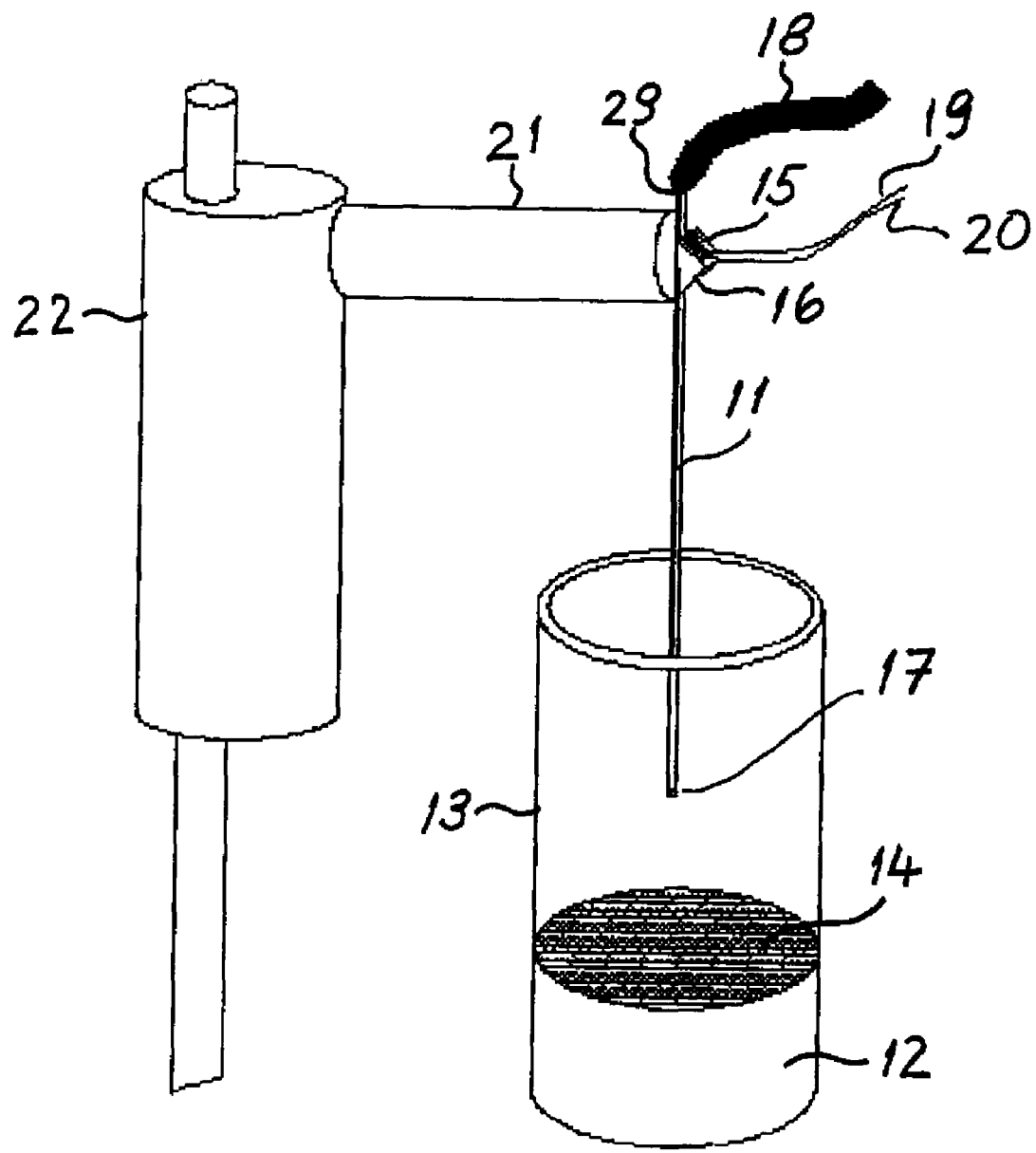
FIG. 1 shows schematically the structure of a pipetting apparatus according to the invention with a pipetting needle at a distance from a liquid in a vessel.

REFERENCE NUMERALS USED IN DRAWINGS 11 pipetting needle
12 liquid
13 vessel
14 surface of liquid
15 electromechanical transducer/piezoelectric transducer
16 coupling member
17 tip of the pipetting needle 18 conduit connected to pipetting needle 11
19 electrical connection lead
20 electrical connection lead
21 arm of X-Y-Z-transport device
22 X-Y-Z-transport device
23 housing part of a needle holder
24 housing part of a needle holder
25 electromechanical transducer/piezoelectric transducer
26 coupling member
27 electromechanical transducer/piezoelectric transducer
28 coupling member
29 end of needle 11 connected to conduit 18
30 length symmetry axis of pipetting needle 11
31 electronic circuit for signal generation and for evaluation of signals corresponding to ultrasonic waves reflected at the tip of the pipetting needle
32 electrical connection lead
33 electrical connection lead
34 electrical connection lead
35 electrical connection lead
41 needle holder
42 housing
43 wall of housing
44 wall of housing
45 movable part of needle holder
46 cavity holding top end part of needle 11
47 electrical connection
48 electrical connector
49 cam disk
50 connection piece for connection with arm 21 of X-Y-Z- transport device 22
51 rotatable knob
52 acoustic lens
53 chamber within movable part 45
54 electrical insulator
55 start-up length
56 spring
57 upper portion of needle 11
58 bore
59 opening
60 base for connector 48
61 ultrasonic sensor
62 transmitter
63 microcontroller and ADC (analog digital converter) circuit
64 receiver
65 high frequency amplifier
66 demodulator and amplifier
67 phase controlled rectifier
68 DAC (digital analog converter) circuit
69 groove in start-up length 55
71 electrical connection between the output of transmitter 62 and ultrasound sensor 61
72 electrical connection between ultrasound sensor 61 and the input of receiver 64
73 output terminal of demodulator and amplifier 66
74 electrical connection between the output of phase controlled rectifier 67 and an input of microcontroller and ADC 63
75 electrical connection between an output of microcontroller and an input of transmitter 62
76 electrical connection between an output of microcontroller and ADC 63 DAC (digital analog converter) 68
77 output terminal of DAC (digital analog converter) 68
81 portion of the raw output signal of ultrasound sensor 61 which correspond to longitudinal vibration modes of pipetting needle 11
82 portion of the raw output signal of ultrasound sensor 61 which correspond to transversal vibration modes of pipetting needle 11
V direction of the wave emitted by the electromechanical transducer, e.g. a piezoelectric transducer
L direction of the reflected wave, vibrating in longitudinal direction as indicated by the double arrow
L' direction of the incident ultrasonic wave, vibrating in longitudinal direction
T direction of the reflected wave, vibrating in transversal direction as indicated by the double arrow
T' direction of the incident ultrasonic wave, vibrating in transversal direction. The shape of the vibration is schematically represented on the left side of FIG. 4 close to the letter T'
$\theta_L$ refraction angle defined by the coupling member 16
$\theta'_L$ refraction angle defined by the coupling member 16
$\theta_T$ refraction angle defined by the coupling member 16
$\theta'_T$ refraction angle defined by the coupling member 16

DETAILED DESCRIPTION

Preferred embodiments are described hereinafter with reference to the accompanying drawings.

Example of a Level Sensor Apparatus According to the Invention

A first embodiment of a level sensor apparatus according to the invention for detecting contact of a pipetting needle with a liquid contained in a vessel is described hereinafter with reference to FIGS. 1 to 5.

Figure 3:
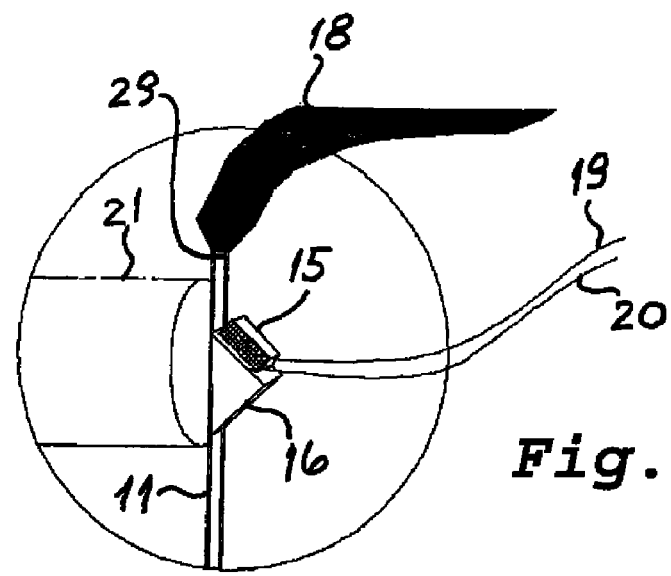
FIG. 3 shows an enlarged view of a portion of FIG. 2.
Figure 2:
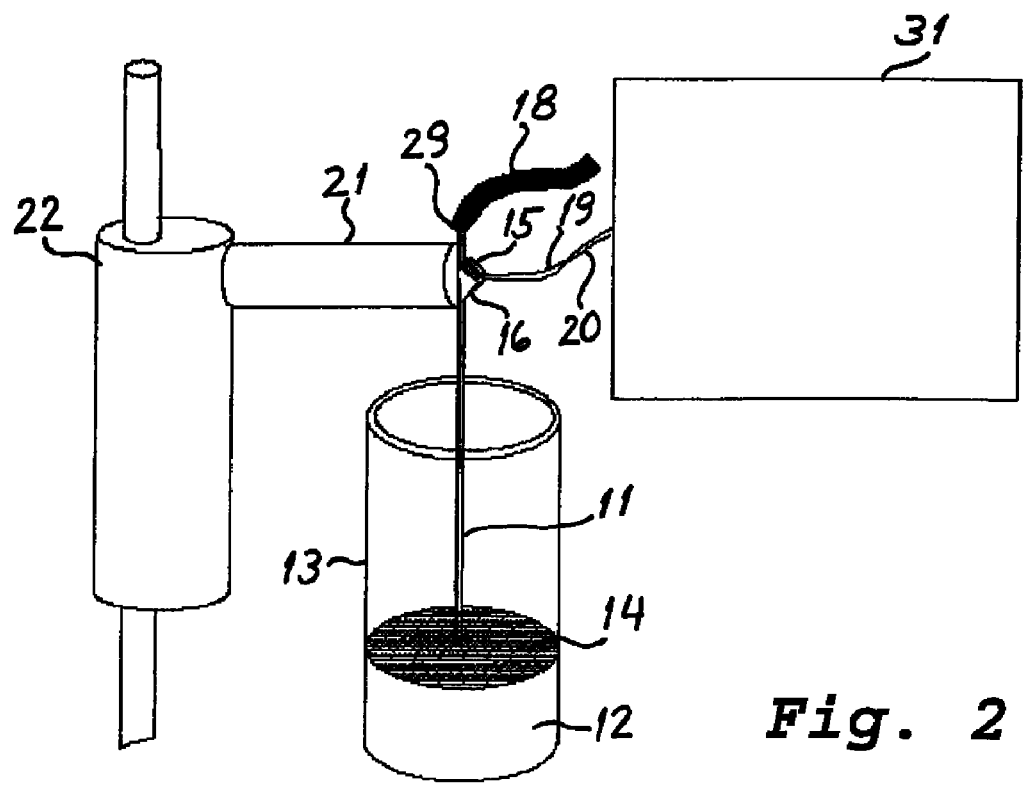
FIG. 2 shows schematically the structure of FIG. 1 when the pipetting needle just enters into contact with a liquid in a vessel.

As shown by FIGS. 1 to 3, the level sensor apparatus comprises a pipetting needle 11, a needle holder at the end of an arm 21 of a X-Y-Z transport device 22, an electromechanical transducer 15, electronic circuit means 31 connected with the electromechanical transducer 15 and transport means 21, 22 for automatically transporting the needle holder and the needle 11.

In the preferred embodiments described hereinafter the electromechanical transducer is e.g. a piezoelectric transducer.

In a preferred embodiment described with reference to FIGS. 1 to 5, the level sensor apparatus comprises a coupling member 16 which is connected to the pipetting needle 11 and to the piezoelectric transducer 15. In another, more simple embodiment of the level sensor apparatus according to the invention the piezoelectric transducer 15 is directly connected to the pipetting needle, e.g. by means of an adhesive material, that is without a coupling member located between piezoelectric transducer 15 and the pipetting needle 11.

A preferred embodiment of level sensor apparatus including a coupling member located between piezoelectric transducer 15 and the pipetting needle 11 is described hereinafter.

Piezoelectric transducer 15, a coupling member 16 and pipetting needle 11 assembled together form an ultrasonic sensor 61 described more in detail hereinafter with reference to FIGS. 6 to 10.

Pipetting needle 11 is made of a material suitable for transmitting ultrasonic waves and has at one end a tip 17 through which liquid is pipetted. The opposite end 29 of needle 11 is connected with a conduit 18 which fluidically connects the pipetting needle with pumping means which make possible to aspirate and to deliver predetermined sample volumes with needle 11.

The needle holder at the end of arm 21 holds pipetting needle 11 and transports it in three directions X, Y, Z which are orthogonal to each other.

Piezoelectric transducer 15 generates ultrasonic pulses to be transmitted towards needle 11, receives echo pulses reflected at the tip 17 of the needle, and generates an electrical output signal representative of the echo pulses. Two terminals 19 and 20 connect piezoelectric transducer 15 to electrical signal generating means 31 and to electrical signal monitoring means 31 which monitor the output signals delivered by piezoelectric transducer 15.

Coupling member 16 is mechanically connected to a part of the needle 11 which is located at a predetermined distance from the tip 17 of the pipetting needle. Coupling member 16 is adapted for applying ultrasonic pulses to the needle 11 and for transmitting to piezoelectric transducer 15 the echo pulses reflected at the tip 17 of the needle.

Electronic circuit means 31 comprise:

electrical signal generating means for generating a driving signal and for applying this signal to the piezoelectric transducer 15, which generates corresponding ultrasonic pulses which are transmitted through the coupling member 16 and the pipetting needle 11 towards the tip 17 thereof, and electrical signal processing means for receiving and processing the electrical output signal of the piezoelectric transducer 15, for selecting at least one specific component of the output signal by means of a time-of-flight or signal phase analysis, and for evaluating the variation with time of predetermined characteristics of a parameter of the at least one selected component of the output signal in order to detect the position of the needle 11 at which the tip 17 of the pipetting needle 11 contacts the free surface 14 of the liquid 12 contained in the vessel 13 and for providing a resulting signal representative of the result of the evaluation.

Transport means 21, 22 transport the needle holder and the needle automatically, position needle 11 at a pipetting position. Transport means 21, 22 are adapted for moving the tip 17 of needle 11 towards and also away from the free surface 14 of the liquid 12 contained in vessel 13.

Figure 4:
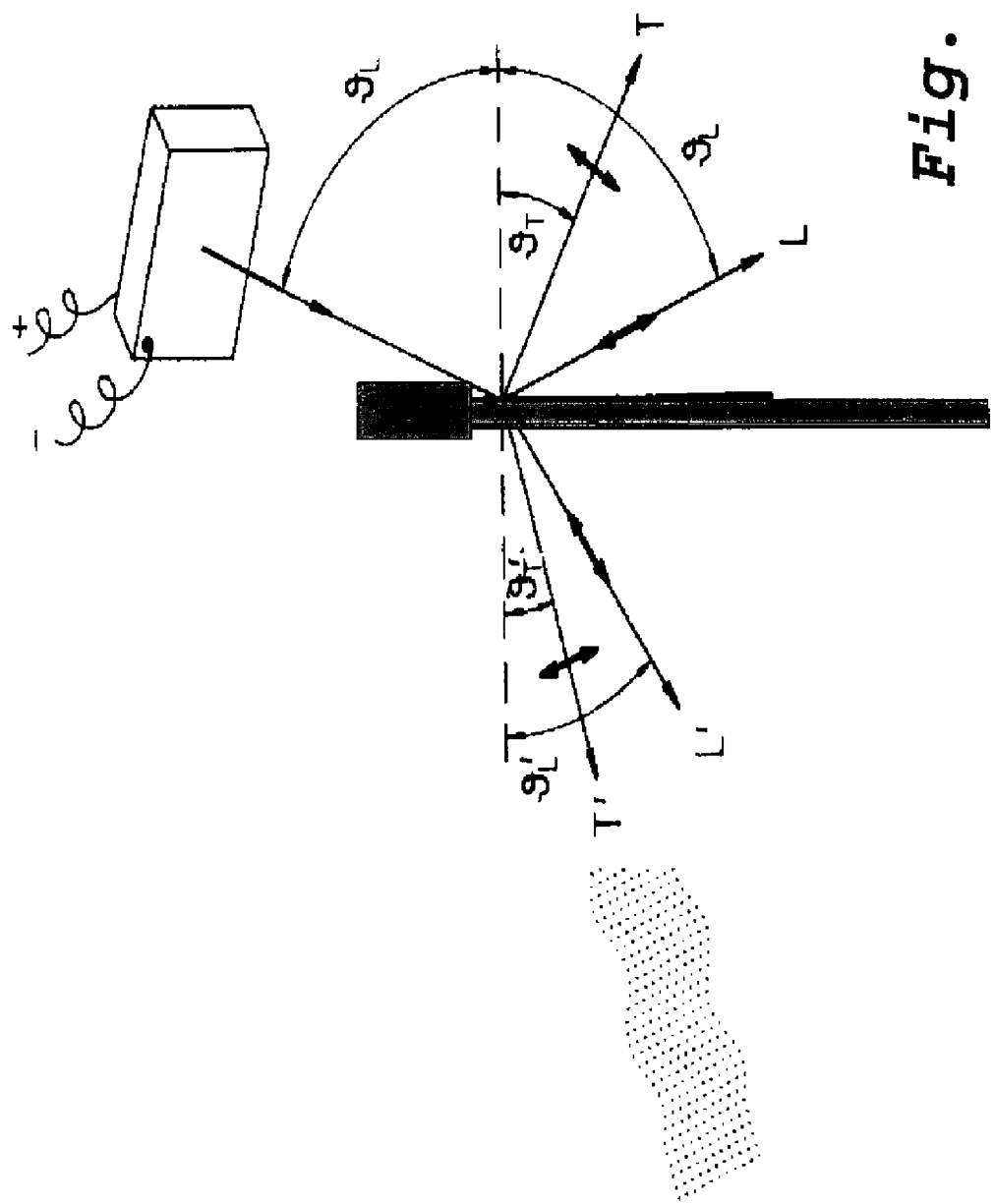
FIG. 4 is a schematic representation of the directions of transmitted and reflected ultrasonic waves that propagate through a pipetting needle.

FIG. 4 shows schematically the directions of transmitted and reflected ultrasonic waves that propagate through a pipetting needle. In FIG. 4 the following directions and angles are represented:

V direction of the wave emitted by the piezoelectric transducer;

L direction of the reflected wave, vibrating in longitudinal direction as indicated by the double arrow;

L' direction of the incident ultrasonic wave, vibrating in longitudinal direction;

T direction of the reflected wave, vibrating in transversal direction as indicated by the double arrow;

T' direction of the incident ultrasonic wave, vibrating in transversal direction. The shape of the vibration is schematically represented on the left side of FIG. 4 close to the letter T';

$\theta_L$ refraction angle defined by the coupling member 16;
$\theta'_L$ refraction angle defined by the coupling member 16;
$\theta_T$ refraction angle defined by the coupling member 16; and
$\theta'_T$ refraction angle defined by the coupling member 16.

Figure 5:
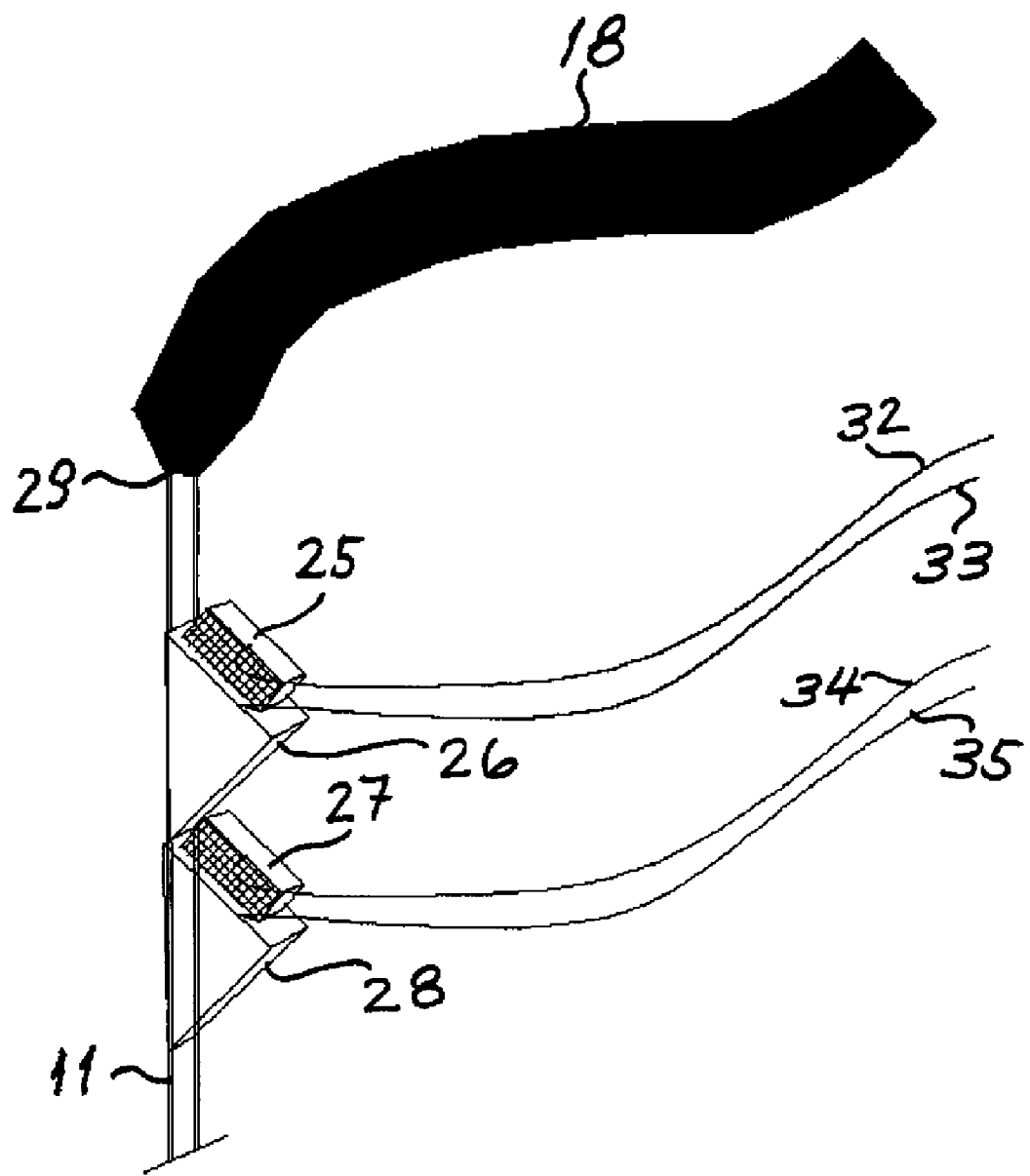
FIG. 5 shows schematically the piezoelectric transducers and coupling members used in a variant of the pipetting apparatus represented in FIG. 1.

In a preferred embodiment shown by FIG. 5 separate transducers and coupling members are used for transmission and for reception of the ultrasonic pulses. A first piezoelectric transducer 25 and a first coupling member 26 connected thereto are used for transmitting ultrasonic waves to needle 11 and a second piezoelectric transducer 27 and a second coupling member 28 connected thereto are used for receiving the ultrasonic echo pulses. Two terminals 32 and 33 connect piezoelectric transducer 25 to electrical signal generating means 31 and to electrical signal monitoring means 31 which monitor the output signals delivered by piezoelectric transducer 25. Two terminals 34 and 35 connect piezoelectric transducer 27 to electrical signal generating means 31 and to electrical signal monitoring means 31 which monitor the output signals delivered by piezoelectric transducer 27.

In a variant of the embodiment shown by FIG. 5, the first piezoelectric transducer 25 and the second piezoelectric transducer 27 are directly connected to pipetting needle 11, i.e. without any coupling member between each transducer and the needle.

In a preferred embodiment the coupling member 16 is adapted for transmitting to the needle 11 the longitudinal wave component of ultrasonic waves emitted by the piezoelectric transducer 15.

In another preferred embodiment the coupling member 16 is adapted for transmitting to the needle 11 the transversal wave component of ultrasonic waves emitted by the piezoelectric transducer 15.

In a preferred embodiment the coupling member 16 is adapted for selectively transmitting to the piezoelectric transducer the longitudinal wave component of ultrasonic echo pulses reflected at the tip 17 of the needle.

In a preferred embodiment the coupling member 16 is adapted for selectively transmitting to the piezoelectric transducer the transversal wave component of ultrasonic echo pulses reflected at the tip 17 of the needle.

In a preferred embodiment electronic circuit means 31 comprise means for evaluating the variation with time of the amplitude or phase of the at least one selected component of the output signal.

In a preferred embodiment the means for evaluating the variation with time of the amplitude and/or phase of the at least one selected component of the output signal according to a predetermined algorithm.

In a preferred embodiment the means for evaluating the variation with time of the amplitude and/or phase of the at least one selected component of the output signal comprise means for detecting changes of the amplitude or phase of a reflected ultrasonic wave and for generating an output signal which corresponds to discontinuities within needle 11 or contact of the needle 11 with an external object or medium.

In a preferred embodiment the means for evaluating the variation with time of the amplitude and/or phase of the at least one selected component of the output signal comprise means for detecting changes of the amplitude or phase of a reflected ultrasonic wave and for generating an output signal which corresponds to the depth of penetration of the tip 17 of needle 11 in the liquid 12 contained in vessel 13.

In a preferred embodiment the piezoelectric transducer 15 and the coupling member 16 are adapted for applying to the pipetting needle 11 ultrasonic pulses which belong to a selected mode of Lamb wave ultrasonic pulses.

Example of a Method According to the Invention

A first embodiment of a method according to the invention for detecting contact of the tip of a pipetting needle with a liquid contained in a vessel, the detecting being effected within a time interval during which the pipetting needle is moved towards the liquid in the vessel for performing a pipetting operation, is described hereinafter.

The method according to this first embodiment is carried out e.g. with a level sensor apparatus of the type described in this specification and comprises:

(a) applying ultrasonic pulses to the pipetting needle 11 by means of a piezoelectric transducer 15 which is mechanically connected to a part of the needle 11 which is located at a predetermined distance from the tip 17 of the pipetting needle 11, (b) transmitting through the pipetting needle 11 mechanical pulses generated by the application of the ultrasonic pulses to the pipetting needle 11, (c) the transmitting of mechanical pulses including transmission of mechanical pulses generated by the transducer 15 towards the tip 17 of the pipetting needle 11 and also transmission in the opposite sense of mechanical pulses reflected at the tip 17, (d) receiving the reflected mechanical pulses with the piezoelectric transducer 15, the piezoelectric transducer 15 thereby generating a corresponding electrical output signal, and (e) monitoring the electrical output signal, selecting at least one specific component thereof by means of a time-of-flight or signal phase analysis and by evaluating the variation with time of predetermined characteristics of a parameter of the at least one selected component of the output signal in order to detect the position of the needle 11 at which the tip 17 of the pipetting needle 11 contacts the free surface 14 of the liquid 12 contained in the vessel 13 and for providing a resulting signal representative of the result of the evaluation.

In a preferred embodiment the ultrasonic pulses are applied to the pipetting needle through a coupling member 16 which is mechanically connected to the needle 11 and to a piezoelectric transducer 15 and the coupling member 16 is connected to a part of the pipetting needle 11 which is located at a predetermined distance from the tip 17 of the pipetting needle. An embodiment of a method according to the invention that includes use of a coupling member located between piezoelectric transducer 15 and pipetting needle 11 is described hereinafter.

In a preferred embodiment ultrasonic pulses having a selected wave vibration mode are applied to the needle 11.

In a preferred embodiment ultrasonic pulses having a longitudinal wave vibration mode are applied to the needle 11.

In another embodiment ultrasonic pulses having a transversal wave vibration mode are applied to the needle 11.

In a preferred embodiment the coupling member 16 selectively transmits to the piezoelectric transducer 15 the longitudinal wave component of ultrasonic echo waves reflected at the tip 17 of the needle 11.

In another embodiment the coupling member 16 selectively transmits to the piezoelectric transducer 15 the transversal wave component of ultrasonic echo waves reflected at the tip 17 of the needle 11.

In a preferred embodiment the selecting of at least one specific component of the output signal comprises selecting at least one component thereof which corresponds to a predetermined longitudinal wave mode of the reflected mechanical pulses.

In another embodiment the selecting of at least one specific component of the output signal comprises selecting at least one component thereof which corresponds to a predetermined transversal wave mode of the reflected mechanical pulses.

In a preferred embodiment the at least one specific component of the output signal is selected by a fixed time-of-flight value of the received output signal.

In a further preferred embodiment the selecting of the at least one specific component of the output signal comprises selecting a first component thereof which corresponds to a longitudinal wave mode of the reflected mechanical pulses and a second component of the output signal which corresponds to a transversal wave mode of the reflected mechanical pulses. In a preferred embodiment the first component is selected by a first fixed time-of-flight value of the received output signal and the second component is selected by a second fixed time-of-flight value of the received output signal. These embodiments offer the advantage of a higher reliability and accuracy of the detection of contact between the tip 17 of the pipetting needle 11 and the free surface 14 of the liquid 12 in vessel 13.

In a preferred embodiment the evaluating comprises evaluating the variation with time of the amplitude and/or phase of the at least one selected component of the output signal.

In a preferred embodiment the evaluating comprises comparing the amplitude and/or phase of the at least one selected component of the output signal with predetermined values for detecting contact of the tip 17 of the pipetting needle 11 with a liquid 12 contained in a vessel 13 and/or foam lying above the liquid 12 and/or a cap which closes an opening of the vessel.

In a preferred embodiment the ultrasonic pulses applied to the pipetting needle 11 belong to a selected mode of Lamb wave ultrasonic pulses.

Example of a Needle Holder for a Level Sensor Apparatus According to the Invention An example of a needle holder for a level sensor apparatus according to the invention is described hereinafter with reference to FIGS. 6 to 10.

Figure 6:
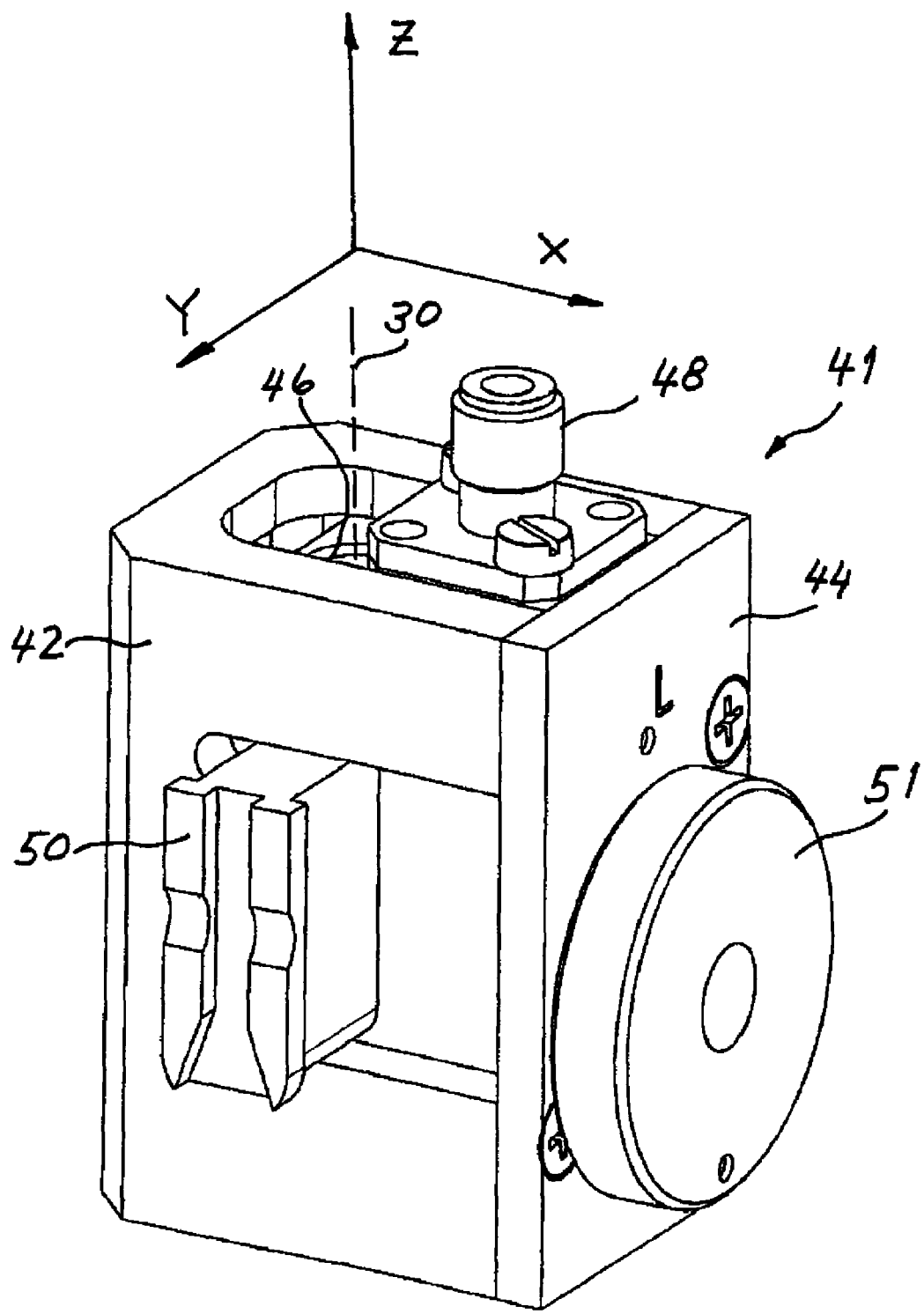
FIG. 6 shows a perspective view of a needle holder 41.

FIG. 6 shows a perspective view of a needle holder 41 which comprises a housing 42. Housing 42 has a connection piece 50 for connecting needle holder 41 to the arm 21 of an X-Y-Z transport device for moving needle holder 41 and thereby pipetting needle 11 in three directions X, Y, Z orthogonal to each other. Needle holder 41 includes an electrical connector 48 which connects an ultrasonic sensor 61 (not shown in FIG. 6) with electronic circuit 31 in FIG. 2. Needle holder 41 further comprises a rotatable knob 51 for adjusting the position of a movable part 45 (not shown in FIG. 6) arranged within housing 42. Rotatable knob 51 is adjacent to a side wall 44 of needle holder 41. The length symmetry axis 30 of a pipetting needle 11 installed within needle holder 41 is aligned with the Z-axis of coordinate axis X, Y, Z represented in FIG. 6.

Figure 7:
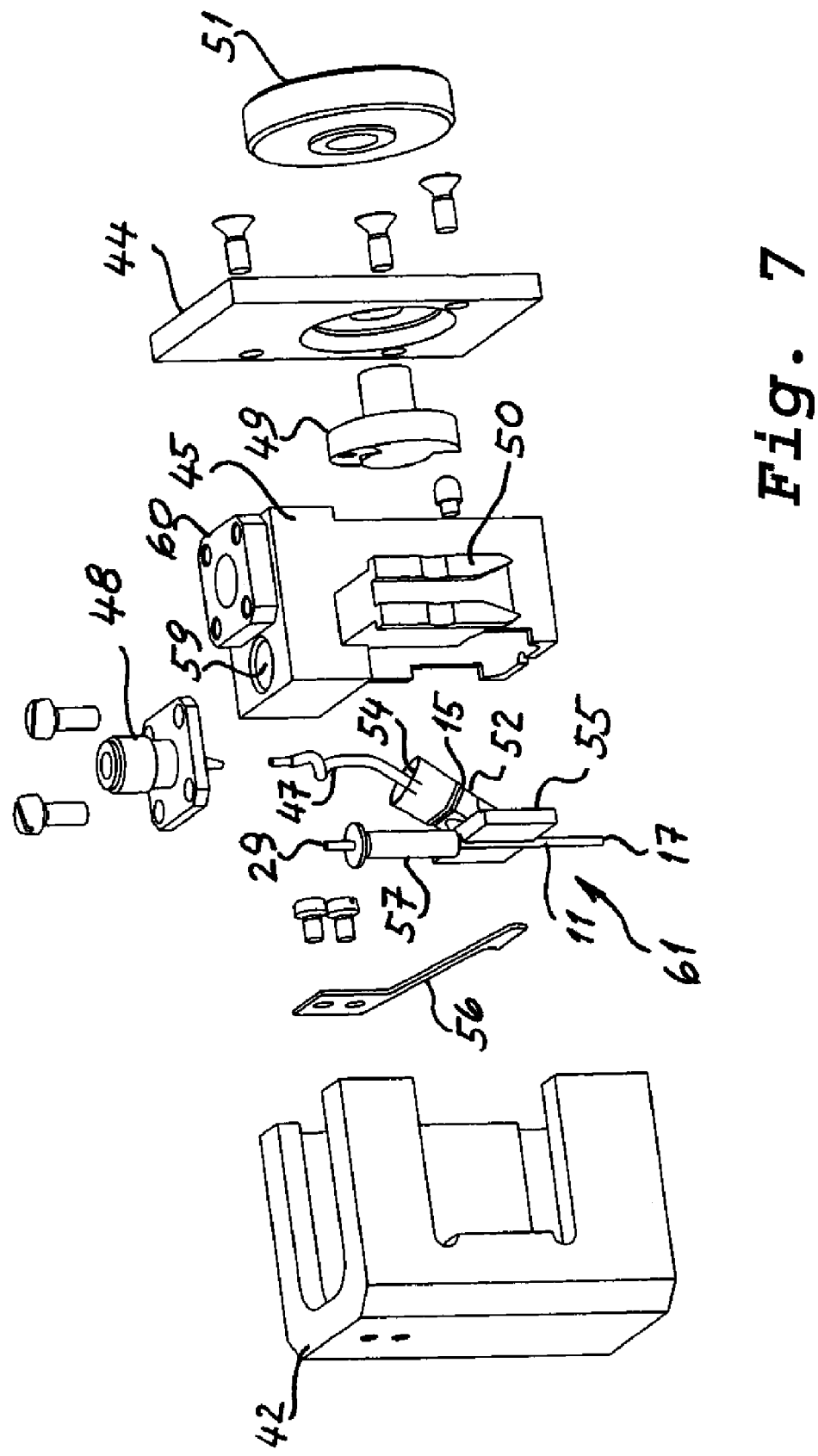
FIG. 7 shows a perspective exploded view of the components of needle holder 41 in FIG. 6.

FIG. 7 shows a perspective exploded view of the components of needle holder 41 in FIG. 6. In addition to parts already described above with reference to FIG. 6, FIG. 7 shows the following components which are arranged within housing 42: a spring 56, a movable part 45, a cam disk 49, an ultrasonic sensor 61 comprising a piezoelectric transducer 15, an acoustical lens 52, a start-up length 55 and the lower portion of pipetting needle 11 which ends in tip 17 thereof. Acoustical lens 52 which is made e.g. of aluminum, and start-up length 55 which is made e.g. of Plexiglas® acrylic resin form a coupling member 16 as the one shown in FIGS. 1 to 3 which is connected to piezoelectric transducer 15 and to pipetting needle 11. Movable part 45 has an opening 59 which allows the introduction of pipetting needle and comprises a base 60 on which electrical connector 48 is mounted.

Figure 8:
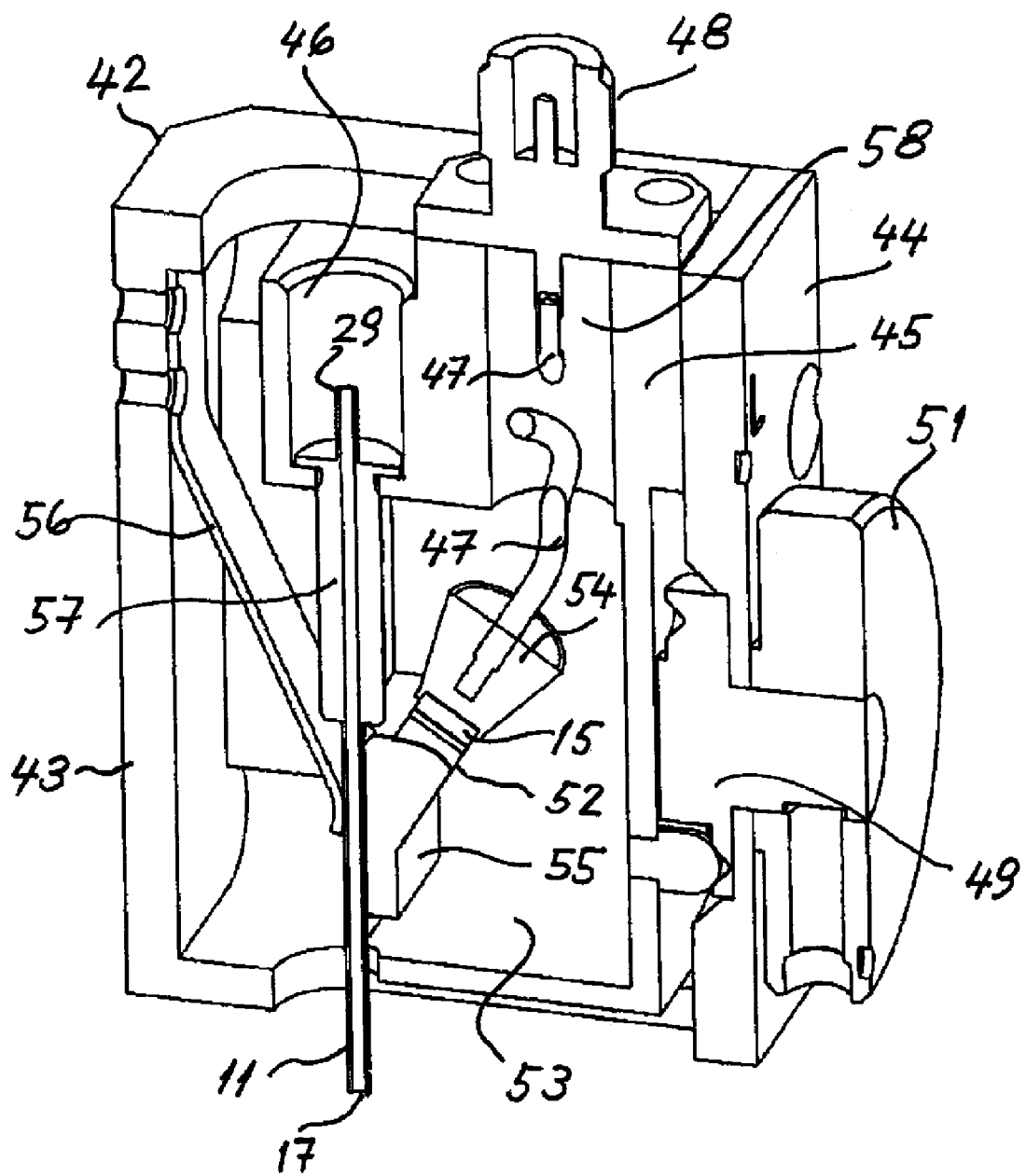
FIG. 8 is a perspective cross-sectional view of needle holder 41 in FIG. 6.
Figure 9:
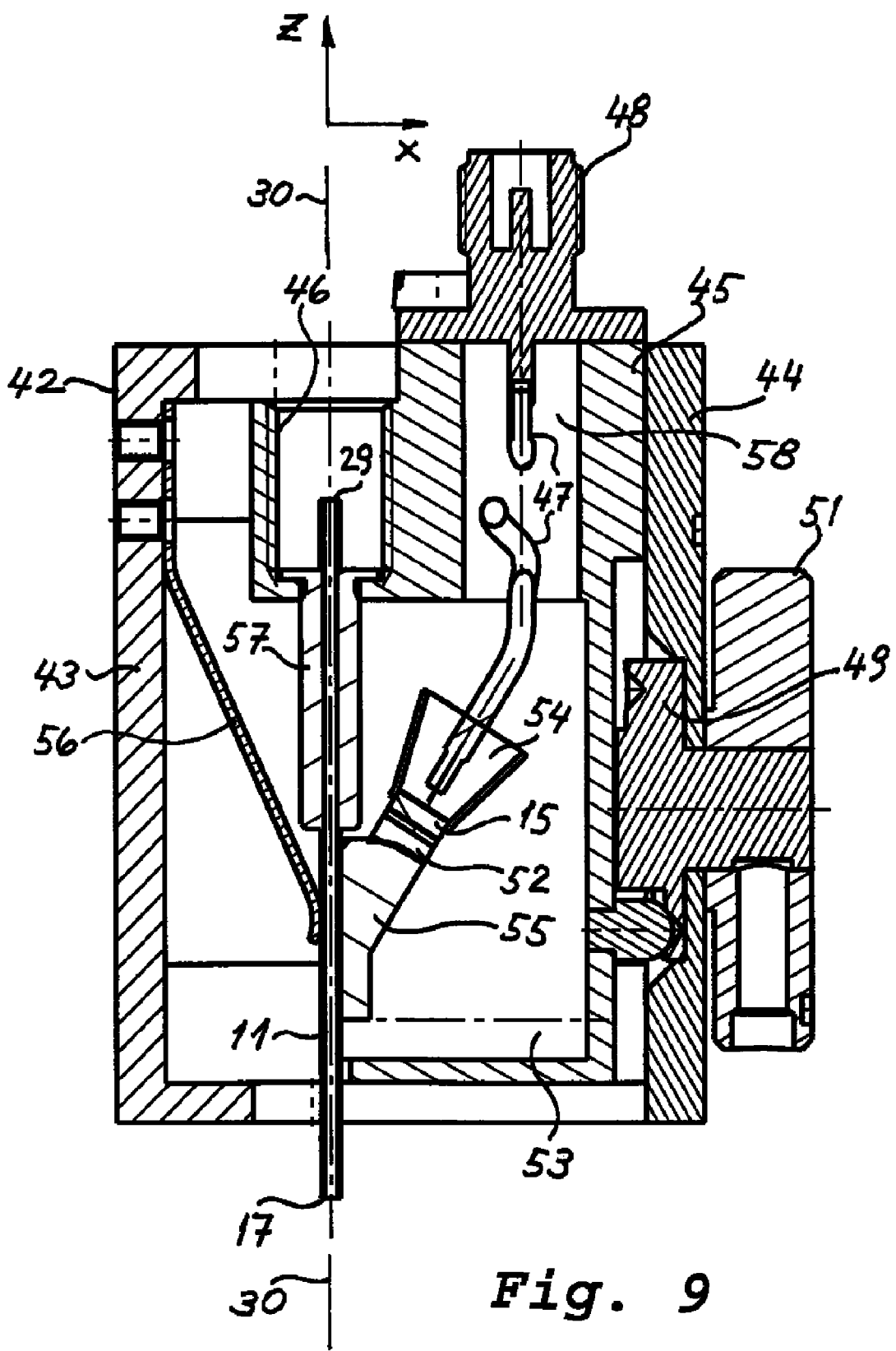
FIG. 9 is a cross-sectional view of needle holder 41 in FIG. 6.

FIG. 8 is a perspective cross-sectional view of needle holder 41 in FIG. 6. FIG. 9 is a cross-sectional view of needle holder 41 along plane X-Z represented in FIG. 6. In addition to parts already described above with reference to FIGS. 6 and 7, FIGS. 8 and 9 shows how pipetting needle 11 and ultrasonic sensor 61 are arranged within movable part 45. FIGS. 8 and 9 show that the upper portion of spring 56 is mounted on wall 43 of housing 42 of needle holder 41 and that the lower part of spring 56 is arranged for exerting a pressure on one side of pipetting needle 11. The position of movable part 45 and thereby the position of needle 11 in X-direction is adjustable by adjusting the angular position of cam disk 49 by means of rotatable knob 51. Rotation of knob 51 and thereby of cam disk 49 in a first sense displaces movable part 45 and thereby needle 11 towards spring 56 and thereby brings needle 11 to its operating position within needle holder 41. Rotation of knob 51 and thereby of cam disk 49 in a second sense opposite to the first sense displaces movable part 45 and thereby needle 11 away from spring 56 and allows removal of needle 11 from its position in movable part 45.

Movable part 45 has a chamber 53 which contains ultrasonic sensor 61 formed by the components 15, 52 and 55. Chamber 53 is preferable filled with an electrically conducting pottant which on one side is an acoustical insulation that shields piezoelectric transducer from ultrasonic waves reflected by the walls of the housing 42, and on the other side electrically connect the electrical earth electrode of the piezoelectric transducer 15 with the electrical earth of the level sensor apparatus. The end portion of electrical connection 47 which is in electrical contact with piezoelectric transducer 15 is embedded in an electrical insulator 54.

Figure 10:
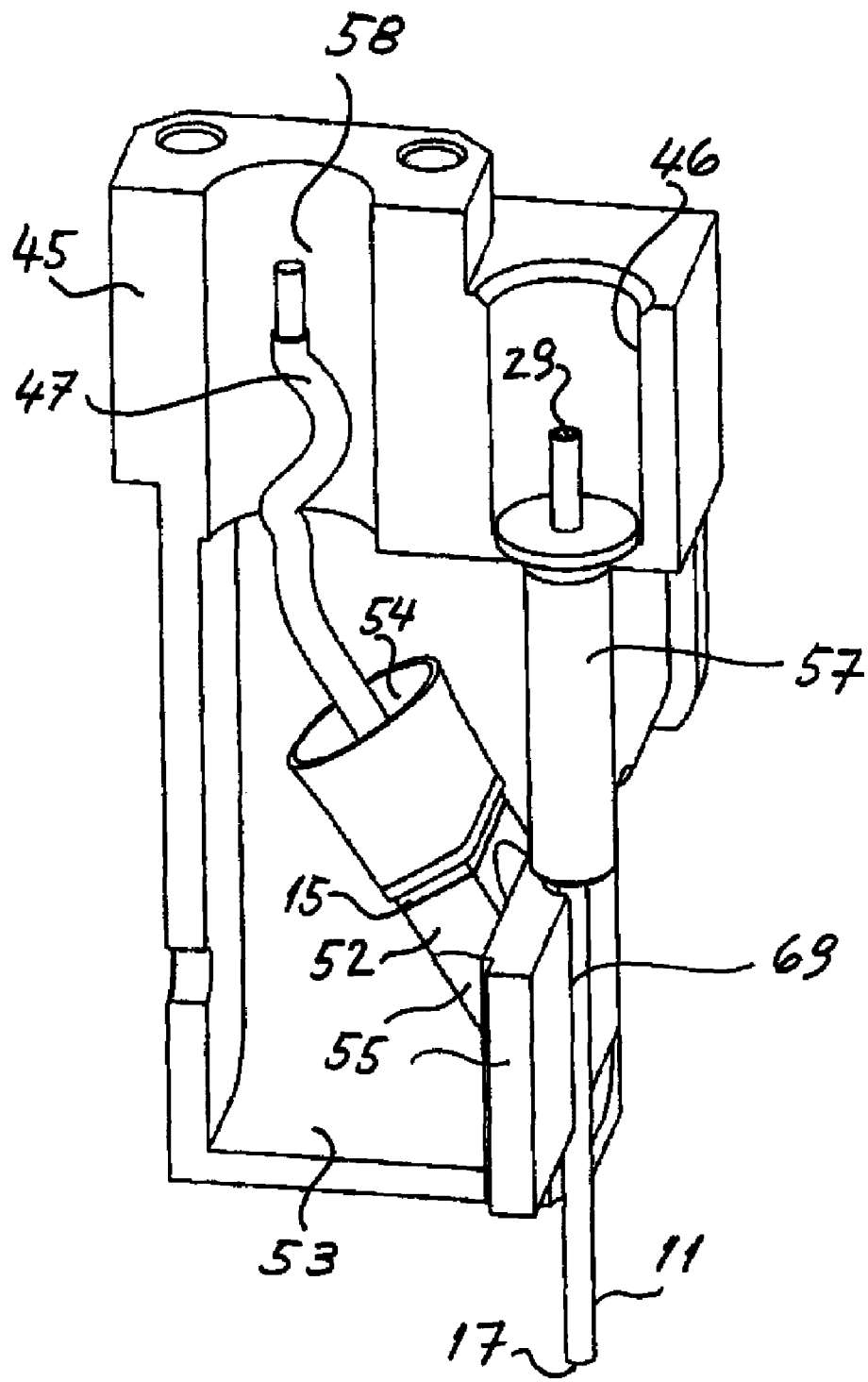
FIG. 10 is a perspective cross-sectional view of the movable part 45 of needle holder 41 in FIG. 6.

FIG. 10 is a perspective cross-sectional view of the movable part 45 of needle holder 41 in FIG. 6. In addition to parts already described above with reference to FIGS. 6 to 9, FIG. 10 shows that the lower part of needle 11 is arranged in a groove 69 in start-up length 55 which is part of coupling member 16. The size of groove 69 is so chosen that about one half of the outer cross-section of needle 11 snuggly fits into groove 69.

Example of an Electronic Circuit for Driving the Piezoelectric Transducer of a Level Sensor Apparatus According to the Invention and for Processing the Output Signal of the Piezoelectric Transducer An example of an electronic circuit for evaluating the output signal of the piezoelectric transducer of a level sensor apparatus according to the invention is described hereinafter with reference to FIGS. 11 to 15.

Figure 11:
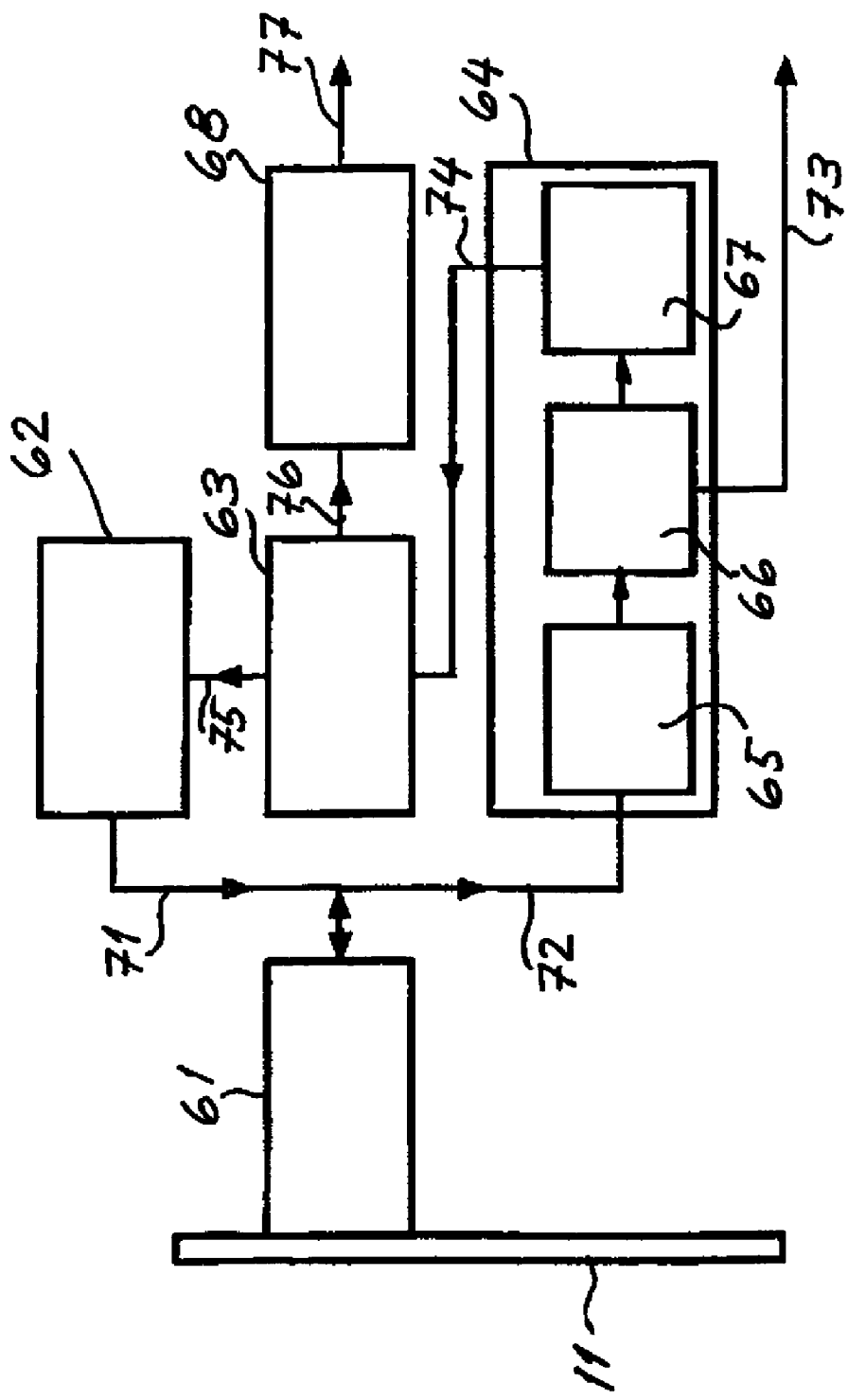
FIG. 11 shows a block diagram showing more in detail the structure of the electronic circuit 31 in FIG. 2.

FIG. 11 shows a block diagram of the electronic circuit 31 in FIG. 2 and also the ultrasonic sensor 61 described above with reference to FIGS. 6 to 10. As shown by FIG. 11 electronic circuit 31 comprises a transmitter 62, a microcontroller and ADC (analog to digital converter) circuit 63, a receiver 64 and a DAC (digital to analog converter) circuit 68.

FIG. 11 shows the following connections between the various blocks: electrical connection 71 between the output of transmitter 62 and ultrasonic sensor 61; electrical connection 72 between ultrasonic sensor 61 and the input of receiver 64; output terminal 73 of demodulator and amplifier 66; electrical connection 74 between the output of phase controlled rectifier 67 and an input of microcontroller and ADC 63; electrical connection 75 between an output of microcontroller and an input of transmitter 62; electrical connection 76 between an output of microcontroller and ADC 63 DAC (digital analog converter) 68; and output terminal 77 of DAC (digital analog converter) 68.

Figure 12:
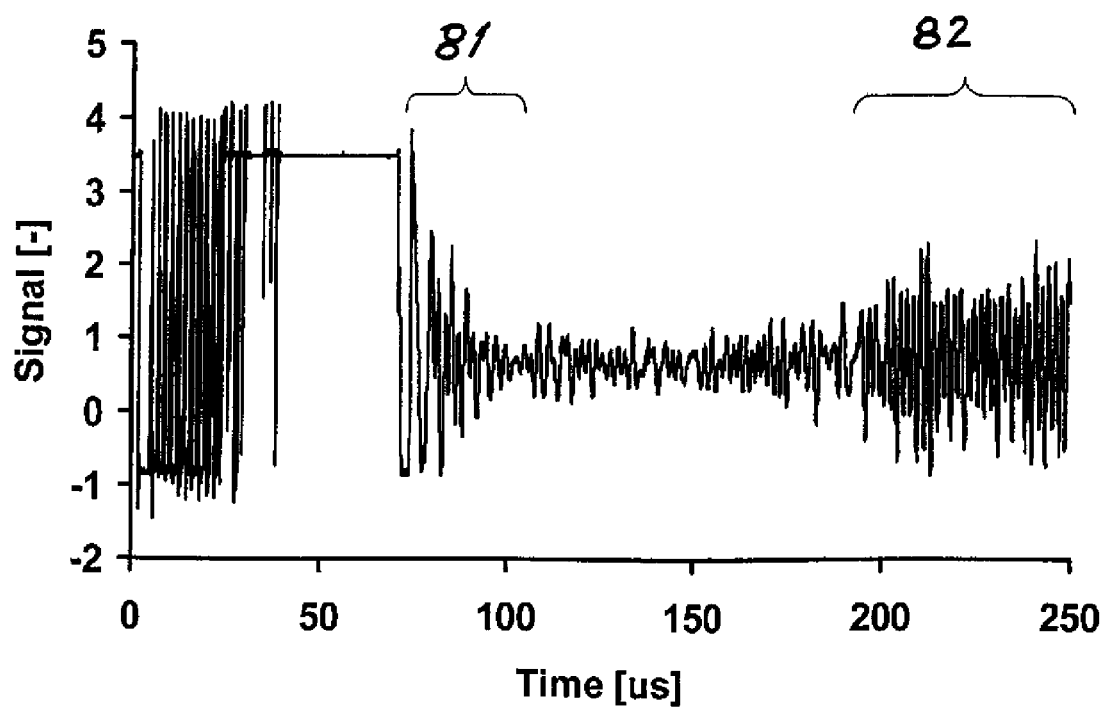
FIG. 12 shows an amplitude vs. time diagram of the raw output signal of ultrasound sensor 61 delivered at output terminal 73 of demodulator and amplifier 66 of receiver 64 in FIG. 11.

FIG. 12 shows an amplitude vs. time diagram of the raw output signal of ultrasonic sensor 61 delivered at output terminal 73 of demodulator and amplifier 66 of receiver 64 in FIG. 11. Portion 81 of the raw output signal of ultrasonic sensor 61 corresponds to longitudinal vibration modes of pipetting needle 11. Portion 82 of the raw output signal of ultrasonic sensor 61 corresponds to transversal vibration modes of pipetting needle 11.

Figure 13:
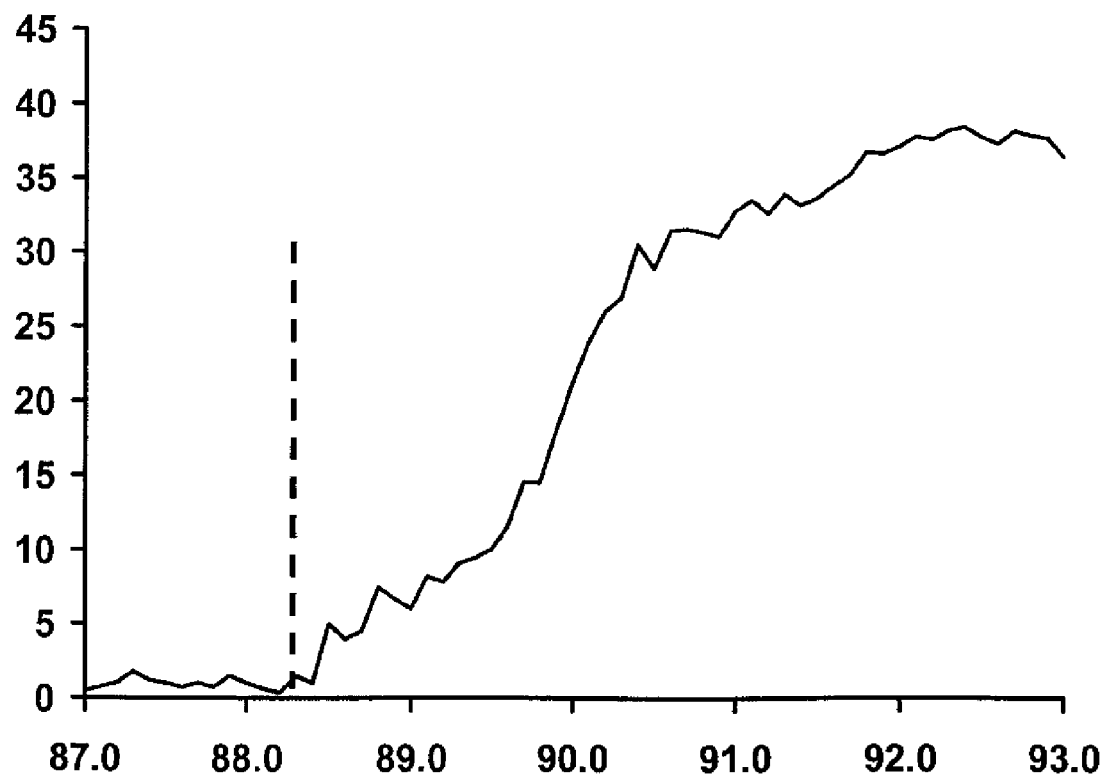
FIG. 13 shows an example of a signal amplitude (vertical axis) vs. needle penetration depth (horizontal axis) diagram obtained for liquid level detection when vessel 13 is open (has no cover) and there is no foam in vessel 13 and the liquid level lies at a needle penetration depth of 88.3 millimeter measured relative to a reference point located above vessel 13, the signal being the liquid level detection signal delivered at output terminal 77 of DAC (digital analog converter) 68.

FIG. 13 shows an example of a signal amplitude (vertical axis) vs. needle penetration depth (horizontal axis) diagram obtained for liquid level detection when vessel 13 is open (has no cover) and there is no foam in vessel 13 and the liquid level lies at a needle penetration depth of 88.3 millimeter measured relative to a reference point located above vessel 13 and indicated with a dashed line on FIG. 13. The signal represented on FIG. 13 is the liquid level detection signal delivered at output terminal 77 of DAC (digital analog converter) 68.

Figure 14:
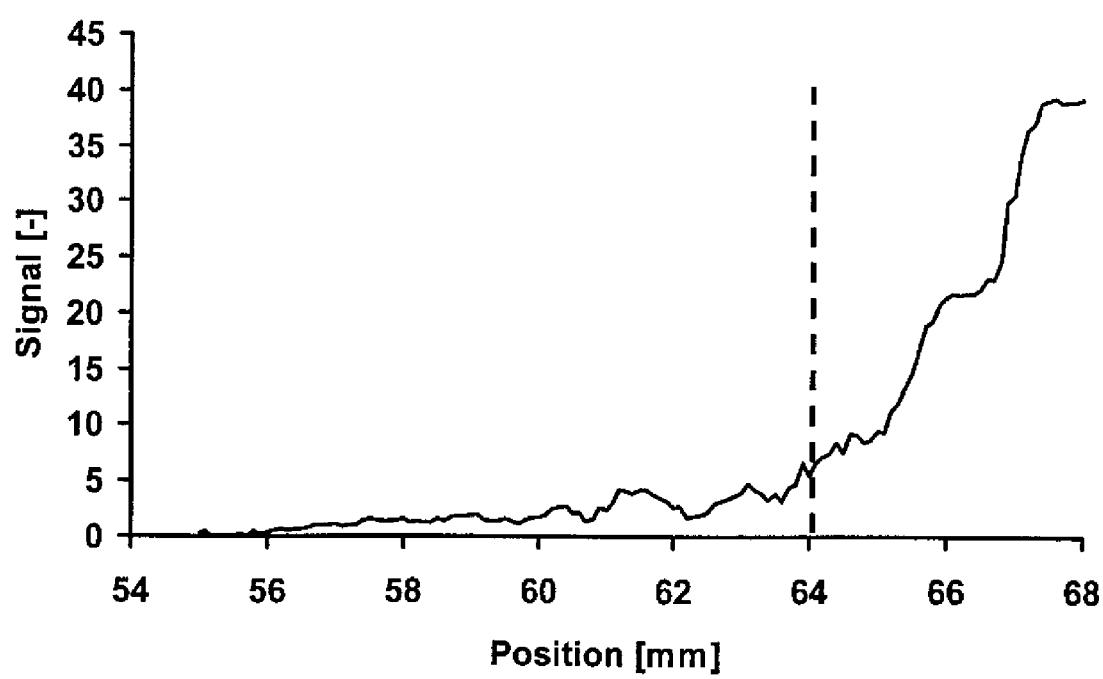
FIG. 14 shows an example of a signal amplitude (vertical axis) vs. needle penetration depth (horizontal axis) diagram obtained for liquid level detection when vessel 13 is open (has no cover), there is foam in vessel 13 and the liquid level lies at a needle penetration depth of 64 millimeter measured relative to a reference point located above vessel 13, the signal being the liquid level detection signal delivered at output terminal 77 of DAC (digital analog converter) 68.

FIG. 14 shows an example of a signal amplitude (vertical axis) vs. needle penetration depth (horizontal axis) diagram obtained for liquid level detection when vessel 13 is open (has no cover), there is foam in vessel 13 and the liquid level lies at a needle penetration depth of 64 millimeter measured relative to a reference point located above vessel 13 and indicated with a dashed line on FIG. 14. The signal represented on FIG. 14 is the liquid level detection signal delivered at output terminal 77 of DAC (digital analog converter) 68.

Figure 15:
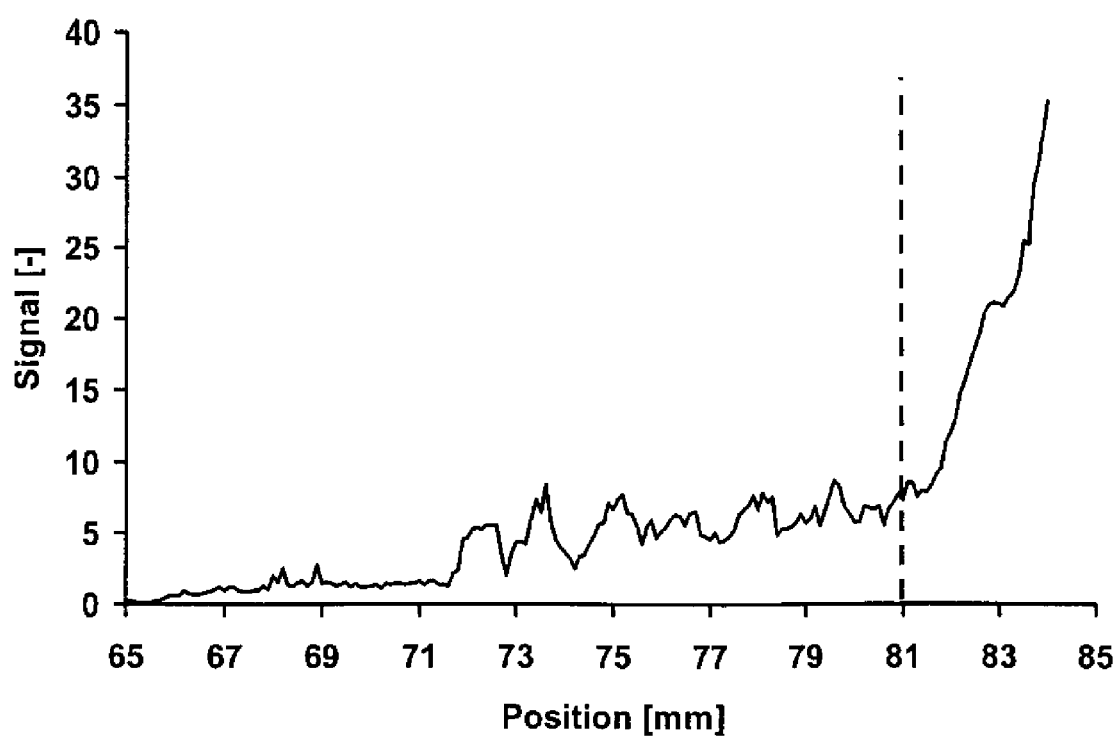
FIG. 15 shows an example of a signal amplitude (vertical axis) vs. needle penetration depth (horizontal axis) diagram obtained for liquid level detection when vessel 13 is closed with a cover (so that pipetting needle pierces the cover of vessel 13 as it moves towards the liquid surface 14 in FIG. 1), there is no foam in vessel 13 and the liquid level lies at a needle penetration depth of 81 millimeter measured relative to a reference point located above vessel 13, the signal being the liquid level detection signal delivered at output terminal 77 of DAC (digital analog converter) 68.

FIG. 15 shows an example of a signal amplitude (vertical axis) vs. needle penetration depth (horizontal axis) diagram obtained for liquid level detection when vessel 13 is closed with a cover (so that pipetting needle pierces the cover of vessel 13 as it moves towards the liquid free surface 14 in FIG. 1), there is no foam in vessel 13 and the liquid level lies at a needle penetration depth of 81 millimeter measured relative to a reference point located above vessel 13 and indicated with a dashed line on FIG. 15. The signal represented on FIG. 15 is the liquid level detection signal delivered at output terminal 77 of DAC (digital analog converter) 68.

In a preferred embodiment, the liquid level detection signal delivered at output terminal 77 of DAC (digital analog converter) 68 is further processed, e.g. by comparing the amplitude of the signal with predetermined threshold values or by comparing the first derivative of the signal amplitude with respect to time with predetermined threshold values, in order to generate a signal indicative of contact of the pipetting needle with the free surface 14 of a liquid 12 in vessel 13. Such a signal is suitable used for an optimized operation of the pipetting unit, e.g. for making sure that for pipetting operations the penetration depth of tip 17 of needle 11 in the liquid 12 is equal to a predetermined minimum value.

Example of a Pipetting Apparatus According to the Invention

A pipetting apparatus according to the invention is an apparatus for pipetting liquid volumes into and from a liquid 12 contained in a vessel 13 by means of a pipetting needle. A pipetting apparatus according to the invention is characterized in that it comprises a level sensor apparatus of the type describe above.

Although preferred embodiments of the invention have been described using specific terms, such description is for illustrative purposes only, and it is to be understood that changes and variations obvious to the skilled artisan are to be considered within the scope of the claims that follow and their equivalents.

What is claimed is:
1. A method for detecting contact of the tip of a pipetting needle with a liquid contained in a vessel, said detecting being effected within a time interval during which the pipetting needle is moved towards said liquid in said vessel for performing a pipetting operation, said method comprising:
   applying ultrasonic pulses to the pipetting needle by means of a electromechanical transducer which is mechanically connected to a part of the needle which is located at a predetermined distance from the tip of the pipetting needle, wherein each of the ultrasonic pulses has a time interval of less than about 250 µs;
   transmitting through the pipetting needle mechanical pulses generated by the application of said ultrasonic pulses to said pipetting needle;
   said transmitting of mechanical pulses including transmission of mechanical pulses generated by said transducer towards the tip of said pipetting needle and also transmission in the opposite sense of mechanical pulses reflected at said tip;

receiving said reflected mechanical pulses with said electromechanical transducer, said electromechanical transducer thereby generating a corresponding electrical output signal; and monitoring said electrical output signal, selecting at least one specific component thereof by means of a time-of-flight or signal phase analysis, and by evaluating the variation with time of predetermined characteristics of a parameter of said at least one selected component of said output signal in order to detect the position of the needle at which the pipetting needle contacts the free surface of said liquid contained in said vessel and for providing a resulting signal representative of the result of said evaluation.

2. A method according to claim 1, wherein said ultrasonic pulses are applied to the pipetting needle through a coupling member which is mechanically connected to the needle and to a electromechanical transducer, said coupling member being connected to a part of the needle which is located at a predetermined distance from the tip of the pipetting needle.

3. A method according to claim 2, wherein said coupling member selectively transmits to the electromechanical transducer the longitudinal wave component of ultrasonic echo waves reflected at the tip of the needle.

4. A method according to claim 1, wherein ultrasonic pulses having a selected wave vibration mode are applied to the needle.

5. A method according to claim 1, wherein ultrasonic pulses having a longitudinal wave vibration mode are applied to the needle.

6. A method according to claim 1, wherein ultrasonic pulses having a transversal wave vibration mode are applied to the needle.

7. A method according to claim 1, wherein said selecting of said at least one specific component of said output signal comprises selecting a component thereof which corresponds to a longitudinal wave mode of said reflected mechanical pulses.

8. A method according to claim 1, wherein said selecting of said at least one specific component of said output signal comprises selecting a component thereof which corresponds to a transversal wave mode of said reflected mechanical pulses.

9. A method according to claim 1, wherein said selecting of said at least one specific component of said output signal comprises selecting a first component thereof which corresponds to a longitudinal wave mode of said reflected mechanical pulses and a second component of said output signal which corresponds to a transversal wave mode of said reflected mechanical pulses.

10. A method according to claim 9, wherein said first component is selected by a first fixed time-of-flight value of the received output signal and said second component is selected by a second fixed time-of-flight value of the received output signal.

11. A method according to claim 1, wherein said at least one specific component is selected by a fixed time-of-flight value of the received output signal.

12. A method according to claim 1, wherein said evaluating comprises evaluating the variation with time of at least one of amplitude and phase of said at least one selected component of said output signal.

13. A method according to claim 12, wherein said evaluating comprises comparing at least one of the amplitude and phase of said at least one selected component of said output signal with predetermined values for detecting contact of the tip of said pipetting needle with at least one of a liquid contained in a vessel, foam lying above said liquid, and a cap which closes an opening of said vessel.

14. A method according to claim 1, wherein the ultrasonic pulses applied to the pipetting needle belong to a selected mode of Lamb wave ultrasonic pulses.

15. A level sensor apparatus for detecting contact of a pipetting needle with a liquid contained in a vessel, said apparatus comprising:

a pipetting needle made of a material suitable for transmitting ultrasonic waves and having at one end a tip through which liquid is pipetted;

a needle holder for holding said pipetting needle, an electromechanical transducer which is mechanically connected to said pipetting needle, said electromechanical transducer being apt to generate ultrasonic pulses to be transmitted to said pipetting needle, wherein each of the ultrasonic pulses persists for about 32 wavelengths or less, to receive echo pulses reflected at the tip of the needle, and to generate an electrical output signal representative of said echo pulses;

electronic circuit means connected with said electromechanical transducer, said electronic circuit means comprising electrical signal generating means for generating a driving signal and for applying this signal to said electromechanical transducer, which generates corresponding ultrasonic pulses which are transmitted to said pipetting needle towards the tip thereof, and electrical signal processing means for receiving and processing said electrical output signal of said electromechanical transducer, for selecting at least one a specific component of said output signal by means of a time-of-flight or signal phase analysis, and for evaluating the variation with time of predetermined characteristics of a parameter of said at least one selected component of said output signal in order to detect the position of the needle at which the tip of the pipetting needle contacts the free surface of said liquid contained in said vessel and for providing a resulting signal representative of the result of said evaluation; and transport means for automatically transporting said needle holder and said needle, for positioning said needle at a pipetting position and for moving the tip of said needle towards the free surface of said liquid contained in said vessel.

16. A level sensor apparatus according to claim 15 which further comprises a coupling member which is connected to the needle and to said electromechanical transducer, said coupling member being mechanically connected to a part of the needle which is located at a predetermined distance from the tip of the pipetting needle, said coupling member being adapted for applying ultrasonic pulses to the needle and for transmitting to said electromechanical transducer said echo pulses reflected at the tip of the needle.

17. A level sensor apparatus according to claim 16, wherein a first electromechanical transducer and a first coupling member connected thereto are used for transmitting ultrasonic waves to said needle and a second electromechanical transducer and a second coupling member connected thereto are used for receiving said ultrasonic echo pulses.

18. A level sensor apparatus according to claim 16, wherein said coupling member is adapted for transmitting to the needle the longitudinal wave component of ultrasonic waves emitted by the electromechanical transducer.

19. A level sensor apparatus according to claim 16, wherein said coupling member is adapted for transmitting to the needle the transversal wave component of ultrasonic waves emitted by the electromechanical transducer.

20. A level sensor apparatus according to claim 16, wherein said coupling member is adapted for selectively transmitting to the electromechanical transducer the longitudinal wave component of ultrasonic echo pulses reflected at the tip of the needle.

21. A level sensor apparatus according to claim 16, wherein said coupling member is adapted for selectively transmitting to the electromechanical transducer the transversal wave component of ultrasonic echo pulses reflected at the tip of the needle.

22. A level sensor apparatus according to claim 16, wherein said electromechanical transducer and said coupling member are adapted for applying to the pipetting needle ultrasonic pulses which belong to a selected mode of Lamb wave ultrasonic pulses.

23. A level sensor apparatus according to claim 15, wherein a first electromechanical transducer is used for transmitting ultrasonic waves to said pipetting needle and a second electromechanical transducer is used for receiving said ultrasonic echo pulses.

24. A level sensor apparatus according to claim 15, wherein said driving signal is a high frequency pulsed signal.

25. A level sensor apparatus according to claim 15, wherein said electronic circuit means comprise means for evaluating the variation with time of at least one of amplitude and phase of said at least one selected component of said output signal.

26. A level sensor apparatus according to claim 25, wherein said means for evaluating the variation with time of at least one of the amplitude and phase of said at least one selected component of said output signal according to a predetermined algorithm.

27. A level sensor apparatus according to claim 25, wherein said means for evaluating the variation with time of at least one of the amplitude and phase of said at least one selected component of said output signal comprise means for detecting changes of the amplitude or phase of a reflected ultrasonic wave and for generating an output signal which corresponds to discontinuities within said needle or contact of the needle with an external object or medium.

28. A level sensor apparatus according to claim 25, wherein said means for evaluating the variation with time of at least one of the amplitude and phase of said at least one selected component of said output signal comprise means for detecting changes of the amplitude or phase of a reflected ultrasonic wave and for generating an output signal which corresponds to the depth of penetration of the tip of said needle in said liquid contained in said vessel.

29. A level sensor apparatus according to claim 15, wherein said electromechanical transducer is adapted for applying to the pipetting needle ultrasonic pulses which belong to a selected mode of Lamb wave ultrasonic pulses.

30. Pipetting apparatus for pipetting liquid volumes into and from a liquid contained in a vessel by means of a pipetting needle, said apparatus comprising a level sensor apparatus according to claim 15.

* * * * *

UNITED STATES PATENT AND TRADEMARK OFFICE
CERTIFICATE OF CORRECTION

PATENT NO.         : 8,100,007 B2                                              Page 1 of 1
APPLICATION NO.    : 12/570319
DATED              : January 24, 2012
INVENTOR(S)        : Elsenhans et al.

It is certified that error appears in the above-identified patent and that said Letters Patent is hereby corrected as shown below:

Title page, Item (57) ABSTRACT, Line 5, "needle, a electromechanical" should read --needle, an electromechanical--;

Col. 12, Line 58, Claim 1, "by means of a electromechanical" should read --by means of an electromechanical--;

Col. 13, Line 21, Claim 2, "and to a electromechanical" should read --and to an electromechanical--.

Signed and Sealed this
Tenth Day of July, 2012

David J. Kappos
*Director of the United States Patent and Trademark Office*